US010702201B2

(12) United States Patent
Vigouroux

(10) Patent No.: US 10,702,201 B2
(45) Date of Patent: Jul. 7, 2020

(54) INSTRUMENTED DEVICE FOR ANALYSING AND QUANTIFYING PHYSIOLOGICAL PARAMETERS OF THE UPPER LIMBS OF A SPORTS PERSON, AND ASSOCIATED METHOD

(71) Applicants: CENTRE NATIONAL DE LA RECHERCHE SCIENTIFIQUE (CNRS), Paris (FR); UNIVERSITÉ D'AIX MARSEILLE, Marseilles (FR)

(72) Inventor: Laurent Vigouroux, Peypin d'Aigues (FR)

(73) Assignees: CENTRE NATIONAL DE LA RECHERCHE SCIENTIFIQUE (CNRS), Paris (FR); UNIVERSITE D'AIX MARSEILLE, Marseilles (FR)

( * ) Notice: Subject to any disclaimer, the term of this patent is extended or adjusted under 35 U.S.C. 154(b) by 124 days.

(21) Appl. No.: 15/576,375

(22) PCT Filed: May 25, 2016

(86) PCT No.: PCT/EP2016/061777
§ 371 (c)(1),
(2) Date: Nov. 22, 2017

(87) PCT Pub. No.: WO2016/189025
PCT Pub. Date: Dec. 1, 2016

(65) Prior Publication Data
US 2018/0344235 A1 Dec. 6, 2018

(30) Foreign Application Priority Data
May 25, 2015 (FR) .................................. 15 54666

(51) Int. Cl.
*A61B 5/22* (2006.01)
*G16H 50/30* (2018.01)
(Continued)

(52) U.S. Cl.
CPC .............. *A61B 5/225* (2013.01); *A61B 5/224* (2013.01); *A61B 5/6895* (2013.01);
(Continued)

(58) Field of Classification Search
CPC ... A61B 5/225; A61B 2503/10; A61B 5/7271; A61B 5/224; A61B 5/6895; G16H 50/30;
(Continued)

(56) References Cited

U.S. PATENT DOCUMENTS

| 8,668,626 B1* | 3/2014 | Horowitz ........... A63B 69/0048 482/35 |
| 9,539,483 B1* | 1/2017 | Tsang ................. A63B 69/0048 |
| 2013/0102440 A1* | 4/2013 | Hutchins ............... A63B 24/00 482/8 |

OTHER PUBLICATIONS

International Search Report as issued in International Patent Application No. PCT/EP2016/061777, dated Jul. 18, 2016.
(Continued)

*Primary Examiner* — Sundhara M Ganesan
(74) *Attorney, Agent, or Firm* — Pillsbury Winthrop Shaw Pittman LLP

(57) ABSTRACT

An instrumented interface for quantifying at least one physiological parameter of the upper limbs of a person, capable of being secured to a gripping device, and including at least one gripping system which the person can hang from, the instrumented interface including at least one force sensor which measures a deformation of the interface when a person exerts a force on the interface via the one gripping device, and is capable of producing a value that translates a force value.

7 Claims, 1 Drawing Sheet

(51) Int. Cl.
| | |
|---|---|
| *A61B 5/00* | (2006.01) |
| *A63B 69/00* | (2006.01) |
| *A63B 23/12* | (2006.01) |
| *A63B 1/00* | (2006.01) |
| *A63B 21/00* | (2006.01) |
| *A63B 71/06* | (2006.01) |
| *H04M 1/725* | (2006.01) |
| *G16H 20/30* | (2018.01) |

(52) U.S. Cl.
CPC .............. *A61B 5/7271* (2013.01); *A63B 1/00* (2013.01); *A63B 23/1218* (2013.01); *A63B 69/0048* (2013.01); *G16H 50/30* (2018.01); *A61B 2503/10* (2013.01); *A63B 21/00047* (2013.01); *A63B 2071/065* (2013.01); *A63B 2071/0625* (2013.01); *A63B 2220/17* (2013.01); *A63B 2220/18* (2013.01); *A63B 2220/51* (2013.01); *A63B 2225/20* (2013.01); *A63B 2225/50* (2013.01); *A63B 2230/01* (2013.01); *G16H 20/30* (2018.01); *H04M 1/725* (2013.01)

(58) Field of Classification Search
CPC .... H04M 1/725; A63B 21/00047; A63B 1/00; A63B 23/1218; A63B 69/0048; A63B 2230/01; A63B 2225/50; A63B 2225/20; A63B 2220/51; A63B 2220/18; A63B 2220/17; A63B 2071/065; A63B 2071/0625
See application file for complete search history.

(56) References Cited

OTHER PUBLICATIONS

Fuss, F. K., et al., "Instrumented climbing holds and performance analysis in sport climbing," Sports Technology, vol. 1, No. 6, Jan. 2008, XP055258336, pp. 301-313.

Fuss, F. K., et al., "The Fully Instrumented Climbing Wall: Performance Analysis, Route Grading and Vector Diagrams—A Preliminary Study," The Impact of Technology on Sport II, Oct. 2007, XP055258470, pp. 677-682.

Noé, F., et al., "Influence of steep gradient supporting walls in rock climbing: biomechanical analysis," Gait and Posture, vol. 13, No. 2, Mar. 2001, XP055258485, pp. 86-94.

"The Campus Board," Retrieved from the Internet: URL: <http://www.metoliusclimbing.com/pdf/Campus_Board_Brochure.pdf>, [retrieved on Mar. 17, 2016], Aug. 2014, XP055259114, 2 pages.

* cited by examiner

INSTRUMENTED DEVICE FOR ANALYSING AND QUANTIFYING PHYSIOLOGICAL PARAMETERS OF THE UPPER LIMBS OF A SPORTS PERSON, AND ASSOCIATED METHOD

CROSS-REFERENCE TO RELATED APPLICATIONS

This is the U.S. National Stage of PCT/EP2016/061777, filed May 25, 2016, which in turn claims priority to French Patent Application No. 1554666, filed May 25, 2015, the entire contents of all applications are incorporated herein by reference in their entireties.

TECHNICAL FIELD OF THE INVENTION

The invention relates to the field of training devices specifically intended to improve and quantify physiological parameters defining the performance factors of sports persons, and in particular practitioners of climbing, also commonly called climbers or alternatively rock-climbers.

More specifically, the invention relates to an instrumented device intended to analyse and quantify the physiological parameters defining the performance factors of the upper members of a sports person, and in particular of a climber. The invention also concerns a method for modelling an exercise or effort capacity of the said sports person.

STATE OF THE PRIOR ART

Climbing is a sport which continues to become ever-more popular, in terms of numbers of practitioners, achieved performance and the number of locations for practicing and training. For a practitioner of climbing, or climber, climbing is a "game" which consists in dealing with increasingly complex and physically difficult routes or boulders by improving all one's performance factors, of a psychological and technical nature, and also all one's biomechanical and physiological factors.

Climbing is a sport of balance where one pulls oneself from one hold to another by subjecting climbers' forearms, arms, hands and fingers to very high stresses. Many scientific physiological studies have thus identified that the crucial parameter for the performance of a climber lies in their ability to exert forces with the ends of their fingers, and to resist the fatigue caused by these efforts.

However, despite this knowledge, trainers and climbers do not have any scientific or technical means enabling their performance to be quantified and improved, and in particular the performance of the forearms and arms. The various existing recommendations and analyses are still in fact at a basic level, consisting in performing standard suspension and/or pull-up exercises, on the basis of an assessment based on experience, the literature and/or the feeling of a trainer. The start-of-season and end-of-season training diagnoses, and the standard exercises, are thus not quantified and based on precise, individualised scientific data, but only on feelings relating to a given accomplished performance.

To improve the performance of the arms and the forearms it is known, in addition to climbing walls and boulders, to use specific training tools, such as hang boards or chin-up bars, or campus boards. These two tools consist of a bracket with holds, of different sizes and/or shapes, on which the climber suspends themselves and pulls themselves along. Despite the known benefits of these training tools for the development of climbers' performance, the current tools are not able to provide relevant and measurable data concerning climbers' performance.

DESCRIPTION OF THE INVENTION

Against this background, the invention seeks to provide an instrumented interface for the quantification of at least one physiological parameter of an individual's upper limbs, which can be securely attached on a gripping device having at least one gripping means allowing the said individual to be suspended, where the said instrumented interface is characterised by the fact that it has at least one force sensor measuring a deformation of the said interface when an individual exerts a force on the said interface via the said gripping device, and which can produce a value representing a force value.

The term "physiological parameters" is understood to mean all the quantifiable scientific variables enabling to the physiological abilities of the individual to be defined, i.e. the individual's performance factors.

The term "gripping device" is understood to mean an element comprising one or more gripping means allowing the individual to be suspended, such as for example a beam, a hang board, a chin-up bar or alternatively all devices enabling an individual to be suspended and to perform exercises, such as pull-ups.

Advantageously, the said instrumented interface includes communication means for data transmission and/or reception.

Advantageously, the said instrumented interface includes at least one force sensor measuring a deformation of the said interface when an individual exerts a force on the said interface via the said gripping device, which can produce a value representing a vertical force value.

Another object of the invention is an instrumented device for the quantification of at least one physiological parameter of an individual's upper limbs, characterised by the fact that it includes:
  a gripping device, such as a hang board or alternatively a chin-up bar, including at least one gripping means; where the said gripping means allows an individual to be suspended;
  where an instrumented interface according to the invention co-operates with the said gripping device.

Advantageously, the said gripping device and the said instrumented interface form a monobloc part.

Advantageously, the said instrumented interface is incorporated in the said gripping device.

Another object of the invention is a method for modelling the exercise capacity of an individual's upper limbs, implemented by a smart device, where the said method includes:
  a step of configuration, consisting in receiving at least one message containing a weight value ($I_{weight}$), a value representing a notion of difficulty ($I_{diff}$) and a value representing a gripping technique ($I_{tech}$);
  a step of reception of measuring data consisting in receiving at least one measurement message containing at least one force value associated with a time value transmitted by an instrumented interface according to the invention;
  a step of calculation of at least one physiological parameter representative of the performance of an individual's forearms or arms, from at least the said difficulty value ($I_{diff}$) and a force value associated with a time value;

a step of transmission consisting in transmitting at least one message containing a value representative of a physiological parameter representing the performance of an individual's forearms or arms, calculated in the previous step.

Advantageously, the said method includes, prior to the step of calculation, a step of reception of a message including at least one weight value ($I_{weight}$).

Advantageously, the said weight value ($I_{weight}$) and/or the said value representing a gripping technique ($I_{tech}$) and/or the said value representing a notion of difficulty ($I_{diff}$) is a local value entered by a Man-Machine Interface.

Advantageously, the said weight value ($I_{weight}$) and/or the said value representing a gripping technique ($I_{tech}$) and/or the said value representing a notion of difficulty ($I_{diff}$) is a value received from a remote source via communication means.

Advantageously, the said value representing a notion of difficulty ($I_{diff}$) is a value equal to the gripping thickness of a gripping means or a value relative to the inclination of a gripping means.

Advantageously, the said value representing a gripping technique is chosen in particular from among the gripping techniques known in the climbing field, such as half-crimp grips, slope grips, full-crimp grips, pinch grips, or alternatively from among the various techniques for gripping a chin-up bar such as the various methods of gripping of the wrist (supination, pronation or alternatively neutral), the various methods of positioning of the hands relative to the width of the shoulder (hands wide apart, hands close together, etc).

Advantageously, the said weight value ($I_{weight}$) is measured.

Advantageously, the method includes a step of assistance consisting in transmitting at least one message containing a value relative to a start and an end of an exercise to be performed by the said individual.

Advantageously, the step of calculation consists in calculating:
- an index ($SCORE_{force}$) representative of the force of the forearms, where the index is a function of the said force value associated with a time value, and a function of an equation which is a function of the said value representing a notion of difficulty ($I_{diff}$) and of the selected gripping technique ($I_{tech}$) and/or;
- an index ($SCORE_{resistance}$) representative of the resistance of the individual's forearms, where the index is a function of the said force value associated with a time value and/or;
- an index ($SCORE_{endurance}$) representative of the endurance of the forearms, where the index is a function of the said force value associated with a time value.

Advantageously, the step of calculation consists in calculating:
- an index ($SCORE_{energy}$) representative of the capacity of the said individual to perform a succession of pull-ups, where the index is a function of the said force value associated with a time value and/or;
- an index ($SCORE_{power}$) representative of the power of the individual's arms, where the index is a function of the said force value associated with a time value and of the said weight value ($I_{weight}$) and/or;
- an index ($SCORE_{weight/power\ ratio}$) representative of the said power of the said individual's arms, as a function of the said weight value, where the index is a function of the said force value associated with a time value and of the said weight value ($I_{weight}$);
- an index ($SCORE_{muscle}$) representative of the exercise load generated by the various muscle groups of the said individual, where the index is a function of the said force value associated with a time value and of the said selected gripping technique ($I_{tech}$).

Another object of the invention is a computer-readable recording medium on which a computer program is recorded, containing program code instructions for implementation of the steps of the method according to the invention.

The term "smart device" is understood to mean a device such as a computer, phone, tablet, laptop, smart watch, specialist device, etc.

The term "specialist device" is understood to mean a smart device which is directly integrated in the said instrumented interface, or in the said gripping device.

BRIEF DESCRIPTION OF THE FIGURES

Other characteristics and advantages of the invention will be seen clearly on reading the description below, with reference to the appended figures.

In all the figures the common elements have the same references unless otherwise stipulated.

DETAILED DESCRIPTION OF ONE IMPLEMENTATION

Figure 1:
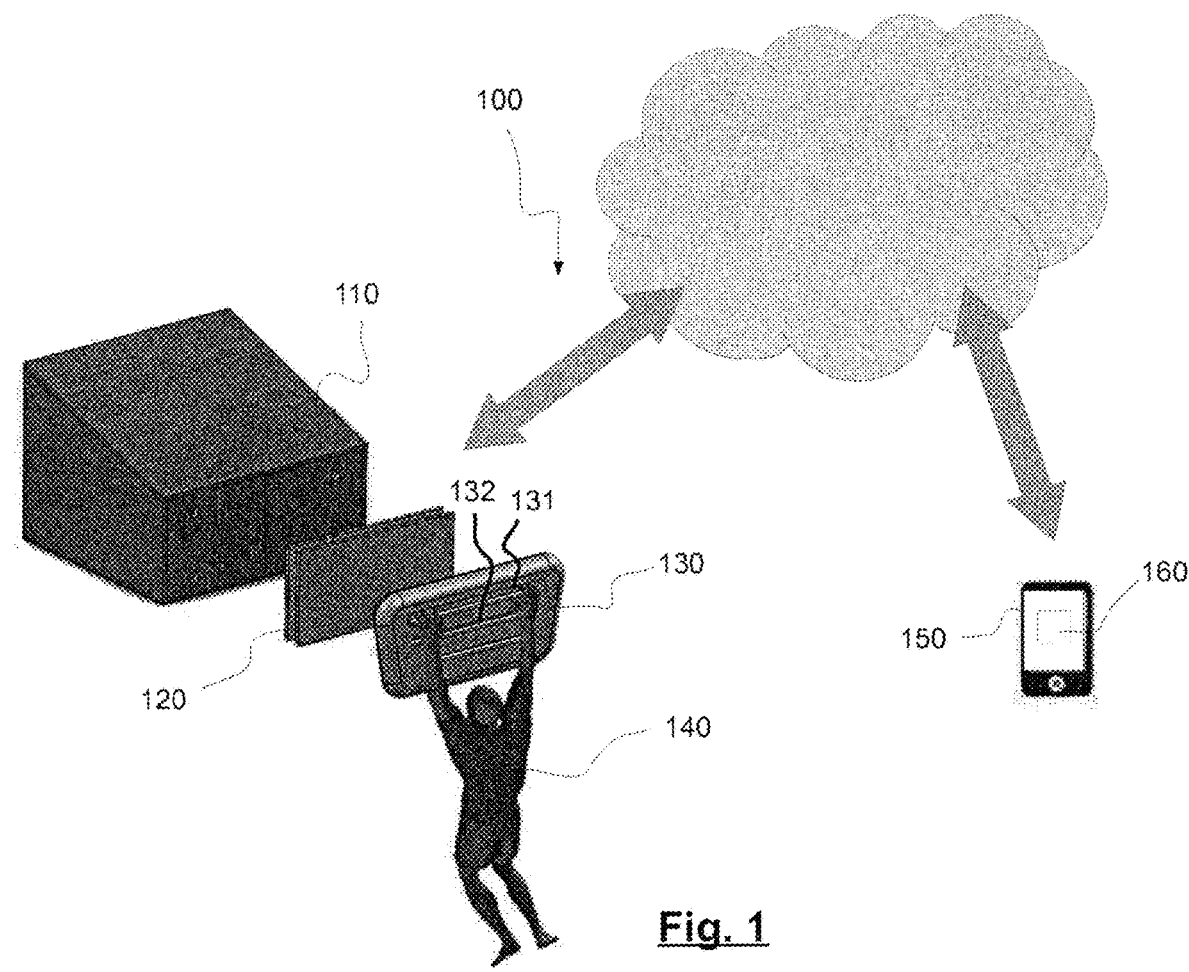
FIG. 1 illustrates diagrammatically an instrumented device for assessing the physiological abilities of an individual's upper limbs, such as an individual practicing climbing.

FIG. 1 illustrates diagrammatically an example implementation of an instrumented device according to the invention enabling the physiological capacities of the upper members of an individual 140 to be analysed, and particularly of a person practicing climbing, a fitness enthusiast or alternatively a body-builder, by quantifying physiological parameters.

Instrumented device 100 according to the invention includes:
- a gripping device formed by a board 130 including at least one gripping means 131, 132; where the said gripping means enables an individual 140, such as a climber, to be suspended from it and/or to perform pull-ups on it, and to exert a roughly vertical force on it;
- an instrumented interface 120, which may for example be positioned between said board 130 and a bracket 110 (illustrated as an example in FIG. 1), able to hold said device 100, where said instrumented interface 120 contains sensors capable of providing a force value, advantageously a vertical force value, for example by measuring a deformation of said interface 120.
- software means 160 able to receive the measurements of the sensors of instrumented interface 120, and able to model the exercise capacity of an individual's upper limbs.

Said instrumented interface 120 also contains means enabling device 100 to be attached to bracket 110.

According to the implementation illustrated in FIG. 1, said instrumented interface 120 is an independent, removable part of said board 130, such that various boards can be interchanged and paired with various gripping means with different shapes and sizes, using a single instrumented interface 120.

According to a second implementation, said instrumented interface 120 and said board 130 are securely attached to one another so as to form a monobloc assembly.

According to a third implementation, said instrumented interface 120 is integrated directly in said board 130.

As represented in FIG. 1, gripping means 131, 132 are formed by holds enabling them to be gripped using one or two hands. The holds of board 130 can have shapes and sizes enabling the possible grips by the climber to be varied.

According to a variant implementation, board 130 contains a plurality of gripping means advantageously having different shapes and sizes. The sizes and shapes of the holds forming the gripping means are advantageously coupled in pairs, such that the climber has an identical hold for each hand.

The holds forming the gripping means can be holds sculpted directly in said board 130, or alternatively separate holds, which can be removable or securely and permanently attached on board 130.

Instrumented interface 120 also contains communication means allowing communication with smart device 150, for example a computer, phone, tablet, laptop, smart watch, specialist device, etc. also containing communication means to dialogue with said instrumented interface 120.

It should be noted that the term "specialist device" is understood to mean a smart device which is directly integrated in said interface 120 or in said board 130.

The communication means consists, for example, of wireless communication means as illustrated in FIG. 1, or any other means allowing the transmission of data.

Smart device 150 contains software means 160 able to implement a method for modelling the physiological capacity or performance of a climber 140 involved when this climber applies a force with their upper limbs, on the basis of data measured by said instrumented interface 120. More specifically, software means 160 enable the physiological parameters representative of performance of the forearms and/or of the arms of a climber to be quantified.

Smart device 150 also contains a Man-Machine interface, and display means to display the results delivered by software means 160.

Device 100 according to the invention thus enables force data correlated with time data from instrumented surface 120 to be collected. This data derived from measurements is then transformed into useful and quantifiable data for a climber or trainer. This transformation is accomplished by means of software means 160.

By virtue of the invention, climbers and/or trainers thus have a quantified and accurate assessment of the physiological parameters representing the performance of a climber's forearms and arms. The results obtained by the software are given in the form of an index or score, for example as a percentage. This data in the form of scores enable it such scores to be compared easily in the course of a training season, or in comparison with other climbers, such as, for example, the best current high-level climbers, where the best current climbers can be used to calibrate a maximum score of 100%.

Such a calibration can of course change over time as changes to the best world performances occur. It is then envisaged to update software means 160 by ad hoc means.

More specifically, software means 160 enable the force, resistance and endurance level (also called continuity level) of a climbing practitioner to be analysed and quantified in the form of an index or score. These three indices thus enable the fingers' capacities for production of force to be targeted according to different levels of fatigue.

The term "force" is understood to mean the ability of an individual to produce force with the ends of their fingers during a short period (of the order of several seconds, not exceeding 30 seconds). The force score $SCORE_{force}$ thus indicates the climber's ability to cross very short and very intense climbing sections with small holds.

The term "resistance" is understood to mean the ability of an individual to make one or more high-intensity efforts (for example between 80% and 100% of maximum force), over a period (of the order of several tens of a second to several minutes) without a decline in performance due to the effects of muscle fatigue. Resistance score $SCORE_{resistance}$ thus indicates the climber's ability to cross climbing sections with a succession of several very difficult movements without any intermediate relaxation (i.e. rest periods).

The term "endurance", or "continuity", is understood to mean the said individual's ability to produce force when the effects of muscle fatigue make themselves felt. Endurance score $SCORE_{endurance}$ thus indicates the climber's ability to cross climbing sections involving a large number of movements with or without intermediate relaxation (i.e. rest periods).

Software means 160 also enables the ability of an individual to perform pull-ups to be assessed by the quantification in the form of an index, or score, of four physiological parameters such as the energy expended by the individual, the power developed by the individual, the individual's weight/power ratio, and the muscular exercise load borne by each muscle group of the said individual.

Energy score $SCORE_{energy}$ is thus representative of the said individual's ability to perform a succession of pull-ups. This ability is required in particular when the climber crosses a climbing section requiring them to pull themselves up using their arms with a large number of movements.

Developed power score $SCORE_{power}$ represents the ability of the climber's arms to pull them up as powerfully and as rapidly as possible. This ability is required in particular during climbing sections requiring fast, dynamic movements and/or dynos (jumps from one hold to another).

Weight/power ratio score $SCORE_{weight/power\ ratio}$ represents the climate's ability (overall) to pull themselves up as powerfully and rapidly as possible using their arms. This ability is sought in particular during fast, dynamic movements and/or dynos (jumps from one hold to another).

Muscular exercise load score $SCORE_{muscle}$ is representative of the exercise load generated by the various muscle groups during the pull-up exercise. The term "supported effort" is understood to mean the force (expressed in Newtons or kilograms) developed by the individual's muscles over the period, together with the maximum peak forces. This exercise load score is given for each muscle group involved in performing the pull-ups, such as for example the elbow's group of flexor muscles, the elbow's group of extensor muscles, the group of muscles of the anterior trunk, and the group of muscles of the posterior trunk.

Figure 2:
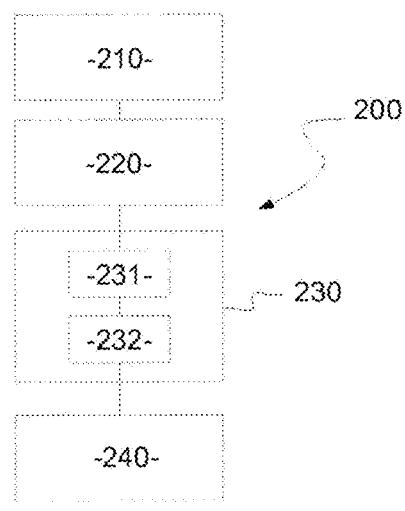
FIG. 2 is a block diagram illustrating the main steps of the method for modelling the exercise capacity of an individual's upper limbs, implemented by a smart device co-operating with the said instrumented device according to the invention.

FIG. 2 is a block diagram illustrating the main steps of the method for modelling the exercise capacity of an individual's upper limbs, implemented by smart device 150, co-operating, via the communication means, with said instrumented device 100 according to the invention.

In a first step 210, called the configuration step, the individual enters configuration parameters, such as a value representing a gripping technique $I_{tech}$ and a value representing a notion of difficulty $I_{diff}$.

The value representing a gripping technique ($I_{tech}$) is chosen from among the gripping techniques known in the climbing field, such as a half-crimp grip, a slope grip, a full-crimp grip, or a pinch grip. The value representing the gripping technique ($I_{tech}$) can also be chosen from among the techniques for gripping a pull-up bar known in the body-building field, i.e. the various methods of gripping with the wrist (supination, pronation or alternatively neutral), together with the various methods of positioning the hands relative to the width of the shoulder (hands wide apart, hands close together, etc).

The value representing a notion of difficulty $I_{duff}$ is for example thickness ep of the hold of the gripping device selected for the assessment. This value could also relate to the number of fingers used, inclination of the hold, etc.

Thus, during this first step 210, the individual selects a type of hold and a gripping technique which will be used to determine the physiological capacities.

During this first configuration step it is also possible to enter a weight value $I_{weight}$. The weight value is equal to the weight of the individual or to their weight loaded with additional masses.

These choices are advantageously made so that the individual is able to take the said hold for a maximum period of between 5 and 15 seconds, advantageously of the order of 10 seconds.

This first configuration step 210 can be accomplished using the Man-Machine interface, for example by the individual directly selecting the configuration parameters. However, this step can also be automated, for example during a step of confirmation, during which the climber keeps themselves suspended for several seconds with the selected hold or holds of board 130, so as to confirm the correct choice of hold, and so as to transmit and enter automatically the configuration parameters relating to weight $I_{weight}$ and possibly to the notion of difficulty $I_{duff}$ by choosing the hold with which the climber keeps themselves suspended.

In a second step 220 the individual follows a programme of exercises, for example a fatigue programme. The type of exercise to be followed during this step depends on the physiological parameters which the individual wishes to quantify, i.e. the parameters representing the performance of the forearms or the performance of the arms.

According to a variant implementation the programme of exercises contains all the exercises required to determine the physiological parameters representative both of the performance of the forearms and of the performance of the arms.

Thus, to quantify and assess the performance of the forearms, the individual follows a programme of "fatigue of the forearms", during which they exert on the selected hold a maximum force for 10 seconds, and then release it for a few seconds, for example 6 seconds. This operation is repeated several times to allow the forearms to become fatigued. Advantageously, this operation is repeated 24 times, corresponding to an exercise lasting 384 seconds.

To quantify and assess the performance of the arms the individual follows a programme of "explosive pull-ups", during which they start with a static suspension lasting several seconds (for example 5 seconds), with the arms stretched, and then perform, within a predetermined time interval, for example between 30 seconds and 1 minute, the highest possible number of pull-ups using the selected hold(s).

When monitoring the exercise programme (fatigue programme or explosive pull-ups programme), the individual can be assisted by the transmission of visual and/or audio messages via the Man-Machine interface, the transmission of messages indicating, for example, the start and/or the end of the various phases of the exercises to be performed.

During this second step 220, instrumented interface 120 measures various values representing a vertical force value applied to board 130, where each force value is associated with a time value.

This data is received by smart device 150 via the communication means. This data can be received in real time when the exercise programme is being performed, or at the end of the programme, in the form of a data packet.

In a third step 230, called the calculation step, software means 160 determines, in the form of a score, at least one physiological parameter representative of the individual's arms and/or forearms.

In a first calculation sub-step 231, software means 160 determines an average maximum force value $Fmax_i$ for each repetition of the exercise programmes, where i represents the index of the repetition.

To accomplish this, software means 160 determines the maximum force value of the repetition, noted pic $F(t)_i$, and determines an average maximum force value of the repetition by calculating the average of the force within a time interval, noted int, centred around the maximum force value pic $F(t)_i$ as follows:

$$Fmoy_i = \frac{1}{int} \sum_{picF(t)-int/2}^{picF(t)+int/2} F(t)_i$$

In a second calculation sub-step 232, software means 160 determines first index $SCORE_{force}$ representative of the maximum force of the individual's forearms, where index $SCORE_{force}$ is a function of the said force value associated with a time value, and a function, for example, of a $4^{th}$ order polynomial equation, which is itself a function of the said value representing a notion of difficulty $I_{duff}$ and selected gripping technique $I_{tech}$ (for example, a half-crimp grip, open-hand grip, full-crimp grip, pinch grip)

Thus, as an example, the first index representing a force score of the forearms is determined by the following relationship:

$$SCOREforce = \alpha \frac{F_{MAX}}{(a \times I_{diff}^4 + b \times I_{diff}^3 + c \times I_{diff}^2 + d \times I_{diff})}$$

where:
- $F_{MAX}$: the highest value of average maximum force values Fmoyi determined for all the repetitions;
- $I_{cuff}$: the value relative to difficulty, i.e. thickness ($e_p$) of the selected hold in our example implementation;
- α, a, b, c, d: specific coefficients which are a function of configured gripping value $I_{tech}$.

Thus, as an example, for a grip of the open-hand type, the first index representing the force score of the individual's forearms is determined by the following relationship:

$$SCORE_{force} = \frac{1000 \times F_{max}}{(-9.74 \times e_p^4 + 98.97 \times e_p^3 - 362.7 \times e_p^2 + 634.2 \times e_p) \times 2}$$

Software means 160 also determines second index $SCORE_{resistance}$ representative of the resistance of the individual's forearms, where index $SCORE_{resistance}$ is a function of the said force value measured by instrumented interface 120 associated with a time value.

This, in a general sense, the second index representing the resistance score of the forearms is determined by the following relationship:

$$SCORE\ resistance = \left(\frac{\sum_{i=1}^{i=n}(Fmax_i) > \beta F_{MAX}}{F_{MAX} \times n}\right) \times \alpha$$

where:

$F_{MAX}$: the highest value of average maximum force values Fmoyi determined for all the repetitions;

α, β: specific coefficients which are a function of configured gripping value $I_{tech}$.

n: number of force repetitions made in the fatigue programme, i.e. 24 in the example described above More specifically, the second index representing the resistance score of the individual's forearms is determined by the following relationship:

$$SCORE\ resistance = \left(\frac{\sum_{i=1}^{i=n}(Fmoy_i) > 0.8F_{MAX}}{F_{MAX} \times 24}\right) \times 1000$$

Software means 160 also determines third index $SCORE_{endurance}$ representative of the endurance of the individual's forearms, where index $SCORE_{endurance}$ is a function of the said force value measured by instrumented interface 120 associated with a time value.

More specifically, the third index representing the endurance score of the forearms is determined by the following relationship:

$$SCORE_{endurance} = \left(\frac{\sum_{i=1}^{i=n}(Fmoy_i) < threshold_{endurance}}{F_{MAX} \times \varphi}\right) \times 1000$$

where:

$threshold_{endurance} = 1.1 \times average\ (minpics\ (Fmoy_i))$ minpics ($Fmoy_i$): the 5 smallest values of average maximum force $Fmoy_i$ exerted during the exercise, i.e. during the repetitions.

φ: number of repetitions in which the average maximum force of the repetition is less than $threshold_{endurance}$ Software means 160 also determines a fourth index $SCORE_{energy}$ representative of the ability of the said individual to perform a succession of pull-ups; where $SCORE_{energy}$ is a function of the said force value measured by instrumented interface 120 associated with a time value.

More specifically, the fourth index representing the score of energy expended is determined by the following relationship:

$$SCORE_{énergie} = \sum_{i=0}^{i=x} pic(W(i))$$

where:

W(i): the energy expended during pull-up i;

x: number of pull-ups performed during the exercise.

Software means 160 also determines a fifth index $SCORE_{power}$ representative of the power of the individual's arms. More specifically, the fifth index representing the power score is determined by calculating the average of the 5 highest power values observed during the exercise.

More specifically, the fifth index representing the power score is determined by the following relationship:

$SCORE_{power} = average(Pics_{max}\ of\ P(F(t)))$ where:

P(F(t)): Power of F(t) during the i repetitions;

$Pics_{max}$: the 5 highest power values observed during the exercise.

Software means 160 also determines a sixth index $SCORE_{weight/power\ ratio}$ representative of the said power of the arms of the said individual as a function of said weight value $I_{weight}$. More specifically, the sixth index representing the score for the weight/power ratio is determined by calculating the ratio between weight value $I_{weight}$ and the average of the 5 highest power values observed during the exercise of the power score, i.e.:

$$SCORE_{weight/power\ ratio} = \frac{I_{weight}}{average(Pics_{max}deP(F(t)))}$$

Software means 160 also determines a seventh index $SCORE_{muscle}$ representative of the pull-up exercise load, where $SCORE_{muscle}$ is a function of the said force value measured by instrumented interface 120 associated with a value for the time and the selected gripping technique ($I_{tech}$). Seventh index $SCORE_{muscle}$ is expressed as a plurality j of $SCORE_{muscle}$, where each $SCORE_{muscle\ group\ j}$ is associated with the exercise load borne by a specific muscle group.

More specifically, the seventh index representing the power score is determined by the following relationship:

$SCORE_{muscle\ group\ j} = k(j, I_{tech}).SCORE_{energy}$ where:

k: specific coefficient which is a function of configured gripping value $I_{tech}$ and of the selected muscle group;

j: index corresponding to the different muscle groups.

In a fourth step 240 software means 160 transmits a message including at least one score calculated above, such that they can be displayed in a display device communicating with software means 160. Advantageously, the display device is the display device of smart device 150.

Instrumented device 100 according to the invention has been described principally to assess and quantify a climber's physiological performance. However, instrumented device 100 can also be used as a training tool in order to perform appropriate training for the scores obtained by each individual. Indeed, software means 160 is designed to generate exercise programmes specific to each individual, on the basis of the scores obtained and the type of training profile sought by the individual.

The invention has been described in particular in the field of climbing; however the invention can also be used in other related fields, in particular for physiological assessment of persons affected by a pathology of the hand, or more generally of the upper limbs. Such a tool would therefore enable a measurable and quantifiable physiological assessment of the individuals to be obtained, and specific physiotherapy programmes to be developed on the basis of the individual's actual physiological abilities.

The invention can also be used in the field of weight-training and fitness. In this case the gripping device described as a climbing board can also easily be replaced by a simple chin-up bar, or alternatively by an advanced chin-up bar which may involve different types of grips and/or different inclinations.

The invention claimed is:

1. A method for modelling an exercise capacity of an individual's upper limbs, implemented by an intelligent device, said method comprising:
    a step of configuration, consisting in receiving at least one message containing a weight value, a value representing a notion of difficulty and a value representing a gripping technique;
    a step of reception of measuring data consisting in receiving at least one measurement message containing at least one force value associated with a time value transmitted by an instrumented interface, said instrumented interface:
        securely attached to a gripping device, the gripping device having at least one gripping system allowing the individual to be suspended, said instrumented interface including at least one force sensor measuring a deformation of said instrumented interface when an individual exerts a force on said instrumented interface via said gripping device, and the at least one force sensor configured to produce a value representing a force value;
    a step of calculation of at least one physiological parameter representative of the performance of an individual's forearms or arms, from at least said difficulty value and a force value associated with a time value;
    a step of transmission consisting in transmitting at least one message containing a value representative of a physiological parameter representing the performance of an individual's forearms or arms, calculated in the previous step.

2. The method for modelling the exercise capacity of an individual's upper limbs according to claim 1, wherein said weight value and/or said value representing a notion of difficulty and/or value representing a gripping technique is a local value entered by a Man-Machine Interface or a value received from a remote source via a communication system.

3. The method for modelling the exercise capacity of an individual's upper limbs according to claim 1, wherein said value representing a notion of difficulty is a value relative to the gripping thickness of the at least one gripping system or a value relative to the inclination of the at least one gripping system.

4. The method for modelling the exercise capacity of an individual's upper limbs according to claim 1, further comprising a step of assistance consisting in transmitting at least one message containing a value relative to a start and an end of an exercise to be performed by said individual.

5. The method for modelling the exercise capacity of an individual's upper limbs according to claim 1, wherein the calculation step consists in calculating:
    an index representative of the force of the forearms, where the index is a function of said force value associated with a time value, and a function of an equation which is a function of said value representing a notion of difficulty and of the selected gripping technique and/or;
    an index representative of the resistance of the individual's forearms, where the index is a function of said force value associated with a time value and/or;
    an index representative of the endurance of the forearms, where the index is a function of said force value associated with a time value.

6. The method for modelling the exercise capacity of an individual's upper limbs according to claim 1, wherein the calculation step consists in calculating:
    an index representative of the capacity of said individual to perform a succession of pull-ups, where the index is a function of said force value associated with a time value and/or;
    an index representative of the power of the individual's arms, where the index is a function of said force value associated with a time value and of said weight value and/or;
    an index representative of said power of said individual's arms, as a function of said weight value, where the index is a function of said force value associated with a time value and of said weight value;
    an index representative of the exercise load generated by the various muscle groups of said individual, where the index is a function of said force value associated with a time value and of said selected gripping technique.

7. A non-transitory computer readable recording medium on which a computer program is recorded which includes program code instructions for the implementation of the steps of the method according to claim 1.

* * * * *